United States Patent [19]

Le Baut et al.

[11] Patent Number: 5,382,593
[45] Date of Patent: Jan. 17, 1995

[54] NEW 3-(HYDROXYBENZYLIDENYL)-INDOLIN-2-ONES

[75] Inventors: Guillaume Le Baut, St Sebastien sur Loire; Marie-Renée Nourrisson, La Chapelle sur Erdre; Jean-Francois Renaud de la Faverie, Le Chesnay; Jean-Guy Bizot Espiard; Daniel-Henri Caignard, both of Paris; Pierre Renard, Versailles; Gérard Adam, Le Mesnil le Roi, all of France

[73] Assignee: Adir et Compagnie, Courbevoie, France

[21] Appl. No.: 94,562

[22] Filed: Jul. 20, 1993

[30] Foreign Application Priority Data

Jul. 21, 1992 [FR] France .................. 92 8951

[51] Int. Cl.⁶ .......................... C07D 209/34
[52] U.S. Cl. .................. 514/418; 514/339; 514/256; 514/414; 548/486; 548/466; 548/467; 548/468; 546/273; 544/333
[58] Field of Search .............. 548/486; 514/418

[56] References Cited

U.S. PATENT DOCUMENTS 5,124,347  6/1992  Connor et al. .................. 514/418

FOREIGN PATENT DOCUMENTS 62029570  7/1985  Japan .

OTHER PUBLICATIONS

Valentine et al. CA 119(11): 117181b. 1992.
Zhungietn et al. CA 78: 111201w 1973.
Nakanishi CA 117(9): 90138n. 1992.
English Abstract of JP 62029570 (1985).
WPIL Derwent Report showing that the Japanese patent has not been extended to other countries.

*Primary Examiner*—Jane T. Fan
*Attorney, Agent, or Firm*—Gordon W. Hueschen

[57] ABSTRACT

The invention relates to a compound selected from those of formula (I):

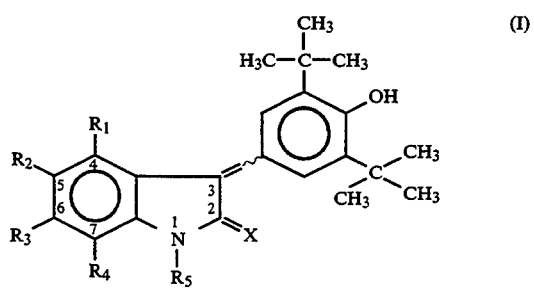

wherein $R_1$, $R_2$, $R_3$, $R_4$, $R_5$ and X are as defined in the description, its Z and E isomers, its optical isomers, in pure form or in the form of a mixture, and its addition salts thereof with a pharmaceutically-acceptable acid or base, and medicinal products containing the same which are useful in treating a disorder resulting from or associated with peroxidation phenomena, disturbances in eicosanoid synthesis, or with platelet aggregation disorders.

8 Claims, No Drawings

NEW 3-(HYDROXYBENZYLIDENYL)-INDOLIN-2-ONES

The present invention relates to new 3-(hydroxy-benzylidenyl)-indolin-2-ones.

The compounds of formula (a), wherein $R_1$ represents a hydrogen atom or a methyl group, are described in a publication by ZHUNGIETU et al (Khim. Geterotsikl. Soedin., 1973, (1): pages 40–44) as reaction products of indoles and hydroxyindole with certain aldehydes, but there is no mention of any pharmacological activity.

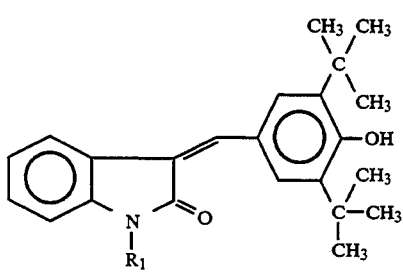

Also known from the prior art are compounds of formula (b):

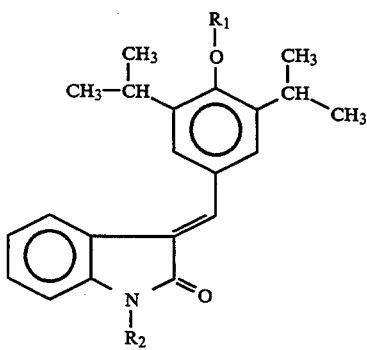

wherein $R_1$ is a hydrogen atom or a benzyl radical and $R_2$ represents a hydrogen atom, a formyl radical, ($C_1$–$C_3$)-acyl or phenyl.

The compounds of formula (b) have been put forward in JP application 62029570 as anti-allergy agents and tyrosine kinase inhibitors.

U.S. Pat. No. 5,124,347 describes compounds with a 3-(3,5-di-tert-butyl-4-hydroxybenzylidenyl)indolinone structure as anti-inflammatory agents.

The Applicant has discovered new 3-(hydroxybenzyl-idenyl)-indolin-2-ones which possess very valuable pharmacological properties.

That is, the new 3-(hydroxybenzylidenyl)-indolin-2-ones of the invention exhibit very significant anti-oxidising properties which are not exhibited by the compounds of U.S. Pat. No. 5,124,347.

More especially, the present invention relates to compounds of formula (I):

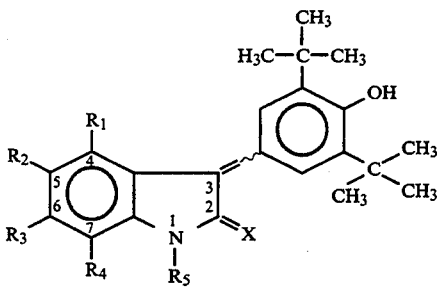

wherein:
X represents a sulphur or oxygen atom,
$R_1$, $R_2$, $R_3$ and $R_4$, which are the same or different, each represents, independently of the others:
 a hydrogen atom,
 or a radical selected from:
  halogen,
  hydroxy,
  a group —$E_1$ or

wherein $E_1$ represents a
 lower alkyl, lower alkenyl, lower alkynyl or lower alkoxy group, it being possible for the group $E_1$ to be unsubstituted or substituted by one or more radicals selected from halogen, lower alkyl, lower alkoxy, lower alkylamino and di-lower alkylamino,
 and a group —$(CH_2)_n$-$E_2$, —O—$(CH_2)_n$-$E_2$,

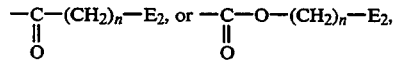

wherein n
 represents O or an integer of from 1 to 4 and wherein $E_2$ is selected from:
 phenyl and naphthyl, each of which is unsubstituted or substituted by one or more radicals selected from halogen, hydroxy, lower alkyl, lower alkoxy and trifluoromethyl,
 and cycloalkyl having from 3 to 8 carbon atoms, which is unsubstituted or substituted by one or more radicals selected from halogen, oxo, lower alkyl and lower alkoxy,
$R_5$ represents a radical selected from:
 hydroxy,
 a group —$E_3$ wherein $E_3$ represents a lower acyl group, a lower alkoxy group, or a —$(CH_2)_n$-CO-$R_6$ group wherein n represents O or an integer of from 1 to 6 and $R_6$ represents a hydroxy or lower alkoxy radical,
it being possible for the group $E_3$ to be unsubstituted or substituted by one or more radicals selected from halogen, hydroxy, lower alkyl and lower alkoxy,
 a phenyl or —O—$(CH_2)_m$-phenyl group wherein m represents O or an integer of from 1 to 4, it being possible for the phenyl nucleus to be unsubstituted or substituted by one or more radicals selected from halogen, hydroxy, lower alkyl, lower alkoxy and trifluoromethyl, a pyridyl or —O—(CH$_2$)$_m$-pyridyl group wherein m is as defined hereinbefore, it being possible for the pyridyl nucleus to be unsubstituted or substituted by one or more radicals selected from halogen, hydroxy, lower alkyl and lower alkoxy,
a group —(CH$_2$)$_m$-E$_4$, —O—(CH$_2$)$_m$-E$_4$ or

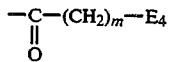

wherein m represents 0 or an integer of from 1 to 4 and E$_4$ is a radical selected from naphthyl, pyrimidinyl, thienyl, furyl and pyrrolyl, E$_4$ being unsubstituted or substituted by one or more radicals selected from halogen, hydroxy, lower alkyl, lower alkoxy and trifluoromethyl, and a cycloalkyl or cycloalkyl-lower alkyl group, wherein the cycloalkyl radical contains from 3 to 8 carbon atoms and is unsubstituted or substituted by one or more radicals selected from halogen, oxo, lower alkyl and lower alkoxy, it being understood that, unless specified to the contrary:

the terms "lower alkyl", "lower alkoxy" and "lower acyl" designate straight-chain or branched groups containing from 1 to 6 carbon atoms, and the terms "lower alkenyl" and "lower alkynyl" represent unsaturated groups having from 2 to 6 carbon atoms, their Z and E isomers, their optical isomers, in pure form or in the form of a mixture, and their addition salts with a pharmaceutically acceptable acid or base.

More especially, the invention extends to compounds of formula (I) wherein R$_5$ represents a lower alkoxy group and to compounds of formula (I) wherein R$_1$, R$_2$, R$_3$ and R$_4$ are selected from hydrogen, halogen, hydroxy, lower alkyl, lower alkoxy and trifluoromethyl, their Z and E isomers, their optical isomers, in pure form or in the form of a mixture, and their addition salts with a pharmaceutically acceptable acid or base.

Of the pharmaceutically acceptable acids that can be used to form an addition salt with the compounds of the invention there may be mentioned by way of example, and without implying any limitation, hydrochloric, sulphuric, phosphoric, tartaric, malic, maleic, fumaric, oxalic, methanesulphonic, ethanesulphonic, campboric and citric acid.

Of the pharmaceutically acceptable bases that can be used to convert the compounds used in accordance with the invention into salts there may be mentioned by way of example, and without implying any limitation, sodium hydroxide, potassium hydroxide, triethylamine, diethylamine, ethanolamine, arginine, lysine and diethanolamine.

The present invention extends also to a process for the preparation of compounds of formula (I) which is characterised in that
a compound of formula (II)

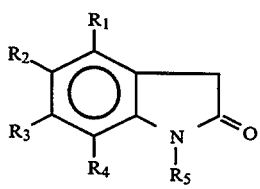

wherein R$_1$, R$_2$, R$_3$, R$_4$ and R$_5$ are as defined for formula (I), is reacted with
a compound of formula (III)

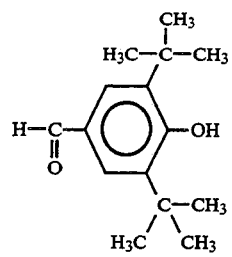

to obtain a compound of formula (I/a)

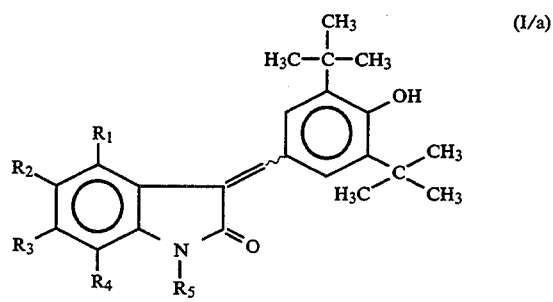

wherein R$_1$, R$_2$, R$_3$, R$_4$ and R$_5$ are as defined for formula (I),
which may be subjected to the action of Lawesson's reagent to yield a compound of formula (I/b)

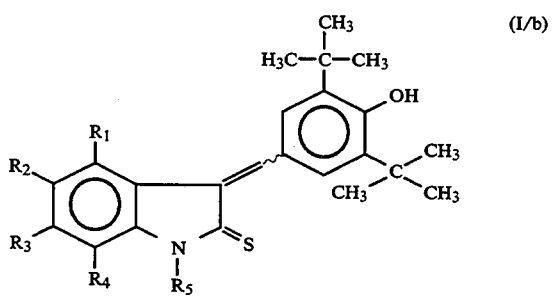

wherein R$_1$, R$_2$, R$_3$, R$_4$ and R$_5$ are as defined hereinbefore,
the compounds of formulae (I/a) and (I/b) forming the totality of the compounds of formula (I),
it being possible for the compounds of formula (I) to be:
purified in accordance with one or more methods of purification selected from crystallisation, chromatography on a silica column, extraction, filtration, and passage through charcoal or resin,
separated, where appropriate, in pure form or in the form of a mixture, into their possible Z and E isomers or their optical isomers,
or converted into salts with a pharmaceutically acceptable acid or base.

The starting materials used in the process described above are either commercially available, or can readily be obtained by the person skilled in the art in accordance with processes known from the literature or proposed in the Preparation Examples described hereinafter in this Application.

The compounds of the present invention exhibit very significant antioxidant properties. Pharmacological studies have in particular shown that the compounds of the present invention have remarkable protective activities in respect of peroxidation processes of cellular lipids and low density lipoproteins (LDLs). Such a level of protective activity was not found for the compounds of U.S. Pat. No. 5,124,347.

Furthermore, the compounds of the present invention exhibit the property of having a powerful inhibiting effect on the biosynthesis of eicosanoids which is far greater than that of the compounds of U.S. Pat. No. 5,124,347. They also exhibit a significant platelet anti-aggregation activity.

The pharmacological activities of the compounds of the invention are also far superior to those of the anti-oxidant compounds of the prior art, especially to that of probucol, a commercially available compound which is known for its antioxidant property and is used therapeutically.

The compounds of the invention, which exhibit the properties of inhibiting lipid peroxidation, eicosanoid biosynthesis and platelet aggregation at the same time, may therefore be expected to have a new and especially beneficial effect in respect of disorders involving peroxidation of membrane lipids, a disturbance in eicosanoid synthesis, or platelet aggregation dysfunctions.

The compounds of formula (I) may thus be used to obtain medicaments for use in the treatment or prevention of disorders resulting from or associated with peroxidation phenomena, disturbances in prostanoid synthesis or platelet aggregation disorders, in the treatment of ischaemic disorders, inflammatory disorders, pain, metabolic disorders, atheroma, arteriosclerosis, respiratory disorders, asthma, emphysema, disorders of immunological origin, psoriasis, lupus erythematosus, allergic reactions, cerebral or peripheral ageing, and in the prevention and treatment of damage resulting from surgical trauma and the reperfusion of organs.

The present invention relates also to pharmaceutical compositions containing at least one compound of formula (I), or an addition salt thereof with a pharmaceutically acceptable acid or base, in combination with one or more pharmaceutically acceptable excipients or carriers.

Of the pharmaceutical compositions according to the invention there may be mentioned by way of example, without implying any limitation, those suitable for oral, parenteral, nasal, rectal, perlingual, ocular or pulmonary administration, and especially injectable preparations, aerosols, eye or nose drops, tablets, which may be film-coated or in the form of dragées, soft gelatin capsules, hard gelatin capsules, suppositories, creams, ointments, and dermal gels.

The dosage varies in accordance with the age and weight of the patient, the route of administration, the nature or the disorder and possible associated treatments, and ranges from 1 mg to 200 mg (preferably from 1 to 50 mg, especially from 1 to 20 mg, for example from 10 to 20 mg) of active ingredient per 24 hours in 1 or 2 administrations.

The preparations described in the following can be used in the synthesis of the compounds of the invention. They do not form part of the invention.

The compounds of the following preparations are synthesised in accordance with processes known to the person skilled in the art and detailed especially in Heterocyclic Compounds, vol. 3, John Wiley and Sons, Inc., New York, pp. 129–146, Julian P. L. et al.

PREPARATION 1: 1-METHOXYINDOLIN-2-ONE

Step A: N-(methoxy)-phenylacetamide

Introduce into a round-bottomed flask 6.8 g (50 mmol) of phenylacetic acid and 4.6 g (55 mmol) of methoxylamine hydrochloride, 5.55 g (55 mmol) of triethylamine and finally 10.83 g (52.5 mmol) of N,N-dicyclohexylcarbodiimide. Dissolve in 150 cm$^3$ of dichloromethane. Stir for 16 hours at room temperature. Remove the precipitate by means of filtration and wash it with dichloromethane. Treat the filtrate with 100 cm$^3$ of 3% HCl, then with 100 cm$^3$ of water and finally with 100 cm$^3$ of 5% NaHCO$_3$.

Purify where necessary by passing over a column of silica using dichloromethane as eluant or recrystallise from diisopropyl ether.

Collect 5.28 g of white crystals (63.9 %).
Melting point: 68° C.
Spectral characteristics:
Infrared: $\nu$cm$^{-1}$: $\nu$C=O: 1760, 1735 $\nu$O—CH$_3$: 2890 $\nu$C=C: 1620, 1615, 1620, 1595

Step B: N-(methoxy)-N-(chloro)phenylacetamide

Dissolve 1.65 g (10 mmol) of N-(methoxy)-phenylacetamide in 30 cm$^3$ of dry chloroform. Place in an ice-bath and maintain at a temperature of 0° C. Subsequently, pour in progressively, using a flask, 1.30 g (1.36 cm$^3$, 12 mmol) of tert-butyl hypochlorite which has previously been dissolved in 20 cm$^3$ of chloroform. Stir at 0° C. for 30 min. Check that the reaction is complete by means of thin-layer chromatography. Evaporate the chloroform in vacuo at 35° C. Keep aluminium foil on the round-bottomed flask during this operation. If passage over a column is desired, protect the column from bright light. Elute with dichloromethane. Collect 1.35 g of pure, faintly coloured, liquid product (67.6%). Melting point: 68° C.

Step C: 1-Methoxyindolin-2-one

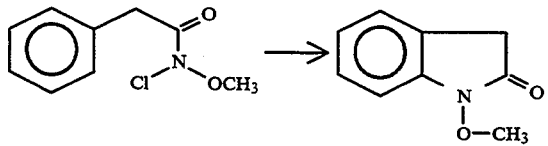

Dissolve 1.35 g (20 mmol) of N-benzylcarbonyl-N-chloro-N-methoxyamine in 20 cm$^3$ of trifluoroacetic acid. Place in an ice-bath to cool, then add a solution of silver carbonate (3.7 g, 20 mmol) in 3 cm$^3$ of trifluoroacetic acid. Stir with a magnetic stirrer for 30 minutes until the reaction is complete. Evaporate the solvent in vacuo below 35° C.

Place the round-bottomed flask once more in an ice-bath, with stirring with a magnetic stirrer. Add a 5% sodium carbonate solution (approximately 100 cm$^3$). Filter the resulting precipitate and wash it with dichloromethane. Extract the aqueous phase (filtrate) with dichloromethane, then treat with a solution of sodium chloride. Dry the organic phase over Na$_2$SO$_4$. Filter, evaporate and purify, if necessary, by passing over a column of silica gel using dichloromethane as eluant. Collect 1.88 g of pure product corresponding to the title compound.

Yield: 57.6%

Melting point: 83° C.

Spectral characteristics:

Infrared: $\nu$ in cm$^{-1}$: $\nu$C=O : 1675 $\nu$O—CH$_3$: 2900 $\nu$C=C : 1650, 1645

PREPARATIONS 2 TO 17

By proceeding as in Preparation 1, but replacing the N-benzylcarbonyl-N-chloro-N-methoxyamine in Step C with a N-benzylcarbonyl-N-chloro-N-methoxyamine appropriately substituted at the benzyl nucleus, the compounds of the following preparations are obtained:

Preparation 2:
1,5,6-TRIMETHOXYINDOLIN-2-ONE

Melting point: 84°–84.5° C.

Preparation 3:
6-CHLORO-1-METHOXYINDOLIN-2-ONE

Melting point: 114°–116° C.

Solvent: DIETHYL ETHER

Preparation 4:
6-BROMO-1-METHOXYINDOLIN-2-ONE

Melting point: 116°–117° C.

Solvent: DIETHYL ETHER

Preparation 5:
1-METHOXY-6-METHYLINDOLIN-2-ONE

Melting point: 64°–65° C.

Solvent: DIETHYL ETHER/HEXANE

Preparation 6:
1-METHOXY-5-BENZYLOXY-INDOLIN-2-ONE

Melting point: 188°–189° C.

Preparation: 7:
4-IODO-1-METHOXYINDOLIN-2-ONE

Melting point: 127°–128° C.

Solvent: DIETHYL ETHER

Preparation 8:
4-FLUORO-1-METHOXYINDOLIN-2-ONE

Melting point: 106°–107° C.

Solvent: DIETHYL ETHER

Preparation 9:
5-CHLORO-1-METHOXYINDOLIN-2-ONE

Preparation 10: 1,5-DIMETHOXYINDOLIN-2-ONE

Preparation 11:
1-METHOXY-4-TRIFLUOROMETHYLINDOLIN-2-ONE

Preparation 12:
1-METHOXY-6-TRIFLUOROMETHYLINDOLIN-2-ONE

Preparation 13:
1-METHOXY-5-METHYLINDOLIN-2-ONE

Preparation 14:
5,6-DIMETHYL-1-METHOXYINDOLIN-2-ONE

Preparation 15:
5-ETHYL-1-METHOXYINDOLIN-2-ONE

Preparation 16:
6-ISOPROPYL-1-METHOXYINDOLIN-2-ONE

Preparation 17:
5-CYCLOPROPYLMETHYL-1-METHOXY-INDOLIN-2-ONE

Preparation 18:
5-CYCLOPROPYLOXY-1-METHOXYINDOLIN-2-ONE

Preparation 19: 1-(PYRID-2-YL)-INDOLIN-2-ONE

Introduce into a 500 cm$^3$ round-bottomed flask 10.50 g (90 mmol) of indole, 375 cm$^3$ of anhydrous dimethylformamide, 17.07 g (108 mmol) of 2-bromopyridine, 41.25 g of copper powder and 90 g of potassium carbonate.

Heat at reflux, with stirring, for 24 hours (the reaction is monitored by thin-layer chromatography in methylene chloride). Filter the reaction mixture to remove the carbonate and the copper. Evaporate the dimethylformamide. A brown doughy product is obtained.

Purify by 2 successive passages over a column of silica gel using a mixture of petroleum ether/ethyl acetate (9/1) and then methylene chloride as eluants. Collect 16.8 g of pale-yellow liquid (96%) corresponding to 1-(pyrid-2-yl)-indole.

Dissolve in methylene chloride the compound obtained in the preceding Step. Place the solution under a nitrogen atmosphere and add thereto, in 4 portions at 30 minute intervals, 103 g (75.3 mmol) of N-chlorosuccinimide. Stir for 1 hour at 15°–20° C. under a nitrogen atmosphere, then pour the reaction mixture into water. Extract with methylene chloride. Dry over Na$_2$SO$_4$. Evaporate to obtain 3-chloro-1-(pyrid-2-yl)-indole.

Dissolve the 3-chloro-1-(pyrid-2-yl)-indole in 1500 cm$^3$ of 2-methoxyethanol and heat to 100° C. with stirring. Add 1100 cm$^3$ of 70% phosphoric acid in a fine stream. Continue heating for 6 hours and then treat the reaction mixture with charcoal under reflux for 15 mins. Filter. Heat to 70° C. while adding 2000 cm$^3$ of water. Cool the precipitated product for 12 hours at 5° C. Filter and dry.

Preparation 20:
1-(4,6-DIMETHYLPYRID-2-YL)-INDOLIN-2-ONE

The title compound is obtained by proceeding as in Preparation 26, but using the appropriately substituted pyridine.

Preparation 21:
1-(2,6-DICHLOROPYL)-INDOLIN-2-ONE

The title compound is obtained after reacting 2-chlorophenylacetic acid and 2,6-dichloroaniline for 2 hours in the presence of potassium carbonate.

Preparation 22: 1-PHENYLINDOLIN-2-ONE

The title compound is obtained by proceeding as in Preparation 21, but replacing the 2,6-dichloroaniline with aniline.

PREPARATIONS 23 TO 27

The compounds of the following Preparations are obtained in accordance with the processes described above:

Preparation 23: 1-ACETYLINDOLIN-2-ONE

Preparation 24: ETHYL 1-[3-(3,5-DI-TERT-BUTYL-4-HYDROXYBEN-ZYLIDENYL)-INDOLIN-2-ONE]-ACETATE Preparation 25: 1-[3-(3,5-DI-TERT-BUTYL-4-HYDROXY-BEN-ZYLIDENYL)-INDOLIN-2-ONE]-ACETIC ACID Preparation 26: 5-CHLORO-1-( PYRID-2-YL )-INDOLIN-2-ONE Preparation 27: 6-CHLORO-1-(2,6-DICHLOROPHENYL)-INDOLIN-2-ONE Preparation 28: 1-(6-METHOXYPYRID-2-YL)-INDOLIN-2-ONE The following Examples illustrate the invention without in any way providing any limitation.

EXAMPLE 1:
6-BROMO-3-(3,5-DI-TERT-BUTYL-4-HYDROXY-BENZYLIDENYL)-1-METHOXY-INDOLIN-2-ONE

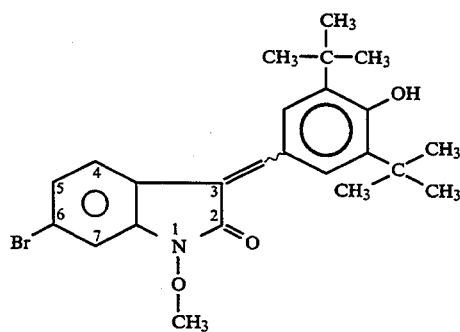

Dissolve 2 g (8.3 mmol) of 6-bromo-1-methoxyindolin-2-one in 25 cm³ of absolute ethanol. Add 2.02 g (8.3 mmol) of 3,5-di-tert-butyl-4-hydroxybenzaldehyde, then 0.5 to 1 cm³ of piperidine. Gently reflux. Monitor the reaction by thin-layer chromatography and discontinue heating after 3 hours' reflux. Evaporate the solvent and purify the resulting product by passing over a column of silica gel using dichloromethane as eluant. Collect first of all the aldehyde that has not reacted and then the title compound.
Yield: 47.4%
Melting point: 132° C.
Recrystallisation solvent: diisopropyl ether/ethanol

EXAMPLE 2:

6-CHLORO-3-(3,5-DI-TERT-BUTYL-4-HYDROXY-BENZYLIDENYL)-1-METHOXY-INDOLIN-2-ONE

The title compound is obtained by proceeding as in Example 1, but replacing the 6-bromo-1-methoxyindolin-2-one with 6-chloro-1-methoxy-indolin-2-one.

Melting point: 165° C.

EXAMPLE 3:

3-(3,5-DI-TERT-BUTYL-4-HYDROXYBEN-ZYLIDENYL)-1-(2,6-DICHLOROPHENYL)-INDOLIN-2-ONE

The title compound is obtained by proceeding as in Example 1, but replacing the 6-bromo1-methoxyindolin-2-one with 1-(2,6-dichlorophenyl)-indolin-2-one.

Yield: 80%

Melting point: 159° C.

Recrystallisation solvent: methylene chloride

EXAMPLE 4:

3-(3,5-DI-TERT-BUTYL-4-HYDROXYBEN-ZYLIDENYL)-1-PHENYLINDOLIN-2-ONE

The title compound is obtained by proceeding as in Example 1, but replacing the 6-bromo1-methoxyindolin-2-one with 1-phenylindolin-2-one.

EXAMPLES 5 TO 19

The compounds of the following Examples are obtained by proceeding as in Example 1 but replacing the 6-bromo-1-methoxyindolin-2-one with the appropriately substituted 1-methoxyindolin-2-one:

EXAMPLE 5:
3-(3,5-DI-TERT-BUTYL-4-HYDROXYBENZYLIDENYL)-1,5,6-TRIMETHOXYINDOLIN-2-ONE

EXAMPLE 6:
3-(3,5-DI-TERT-BUTYL-4-HYDROXYBENZYLIDENYL)-1-METHOXY-6-METHYLINDOLIN-2-ONE

EXAMPLE 7:
3-(3,5-DI-TERT-BUTYL-4-HYDROXYBENZYLIDENYL)-1-METHOXY-5-BENZYLOXYINDOLIN-2-ONE

EXAMPLE 8:
3-(3,5-DI-TERT-BUTYL-4-HYDROXYBENZYLIDENYL)-4-IODO-1-METHOXYINDOLIN-2-ONE

EXAMPLE 9:
3-(3,5-DI-TERT-BUTYL-4-HYDROXYBENZYLIDENYL)-4-FLUORO-1-METHOXYINDOLIN-2-ONE

EXAMPLE 10:
3-(3,5-DI-TERT-BUTYL-4-HYDROXYBENZYLIDENYL)-5-CHLORO-1-METHOXYINDOLIN-2-ONE

EXAMPLE 11:
3-(3,5-DI-TERT-BUTYL-4-HYDROXYBENZYLIDENYL)-1,5-DIMETHOXYINDOLIN-2-ONE

EXAMPLE 12:
3-(3,5-DI-TERT-BUTYL-4-HYDROXYBENZYLIDENYL)-1-METHOXY-4-TRIFLUOROMETHYLINDOLIN-2-ONE

EXAMPLE 13:
3-(3,5-DI-TERT-BUTYL-4-HYDROXYBENZYLIDENYL)-1-METHOXY-6-TRIFLUOROMETHYLINDOLIN-2-ONE

EXAMPLE 14:
3-(3,5-DI-TERT-BUTYL-4-HYDROXYBENZYLIDENYL)-1-METHOXY-5-METHYLINDOLIN-2-ONE

EXAMPLE 15:
3-(3,5-DI-TERT-BUTYL-4-HYDROXYBENZYLIDENYL)-1-METHOXY-5-ETHYLINDOLIN-2-ONE

EXAMPLE 16:
3-(3,5-DI-TERT-BUTYL-4-HYDROXYBENZYLIDENYL)-1-METHOXY-5,6-DIMETHYLINDOLIN-2-ONE

EXAMPLE 17:
3-(3,5-DI-TERT-BUTYL-4-HYDROXYBENZYLIDENYL)-6-ISOPROPYL-1-METHOXY-1-INDOLIN-2-ONE

EXAMPLE 18:
3-(3,5-DI-TERT-BUTYL-4-HYDROXYBENZYLIDENYL)-5-CYCLOPROPYLMETHYL-1-METHOXYINDOLIN-2-ONE

EXAMPLE 19:
3-(3,5-DI-TERT-BUTYL-4-HYDROXYBENZYLIDENYL)-5-CYCLOPROPYLOXY-1-METHOXYINDOLIN-2-ONE

EXAMPLE 20:
3-(3,5-DI-TERT-BUTYL-4-HYDROXYBENZYLIDENYL)-1-(PYRID-2-YL)-1-METHOXYINDOLIN-2-ONE

Introduce into a 100 cm³ round-bottomed flask 2 g (9.5 mmol) of 1-(pyrid-2-yl)indolin-2-one, 40 cm³ of anhydrous benzene, 3.34 g (14.25 mmol) of 3,5-di-tert-butyl-4-hydroxybenzaldehyde and 1 cm³ of piperidine. Heat at reflux with stirring for 3 hours. Evaporate the benzene, and purify the resulting crude product by 2 successive passages over a column of silica gel using methylene chloride as eluant. Collect 1.70 g of yellow powder corresponding to the title compound.

Melting point: 175° C.
Spectral characteristics:
Infrared $\nu cm^{-1}$: $\nu C=O$: 1705 $\nu NH$: 3450 $\nu OH$: 3590

EXAMPLES 21 TO 23

The compounds of the following Examples are obtained by proceeding as in Example 20 but replacing the 1-(pyrid-2-yl)indolin-2-one with the appropriately substituted indolinone.

EXAMPLE 21:
3-(3,5-DI-TERT-BUTYL-4-HYDROXYBEN-ZYLIDENYL)-1-(2,4-DIMETHYLPYRID-6-YL)-INDOLIN-2-ONE

EXAMPLE 22:
3-(3,5-DI-TERT-BUTYL-4-HYDROXYBEN-ZYLIDENYL)-1-(6-METHOXYPYRID-2-YL)-INDOLIN-2-ONE

EXAMPLE 23:
3-(3,5-DI-TERT-BUTYL-4-HYDROXYBEN-ZYLIDENYL)-5-CHLORO-1-(PYRID-2-YL)-INDOLIN-2-ONE

EXAMPLE 24:
3-(3,5-DI-TERT-BUTYL-4-HYDROXYBEN-ZYLIDENYL)-1-METHOXY-INDOLIN-2-ONE

The title compound is obtained by proceeding as in Example 1 but replacing the 6-bromo1-methoxyindolin-2-one with 1-methoxyindolin-2-one.

Melting point: 180° C.
Recrystallisation solvent: diisopropyl ether
Spectral characteristics:
Infrared cm⁻¹: C=O: 1715, 1695 OH: 3610 O—CH₃: 2870 C=C: 1625, 1610, 1595

The compounds of the following Examples are obtained by proceeding as in Example 1, but replacing the 6-bromo-1-methoxyindolin-2-one with the appropriately substituted indolinone:

EXAMPLE 25:
1-ACETYL-3-(3,5-DI-TERT-BUTYL-4-HYDROXY-BENZYLIDENYL)-INDOLIN-2-ONE

Melting point: 152° C.

EXAMPLE 26: ETHYL 1-[3-(3,5-DI-TERT-BUTYL-4-HYDROXY-BEN-ZYLIDENYL)-INDOLIN-2-ONE]ACETATE

EXAMPLE 27:
1-[3-(3,5-DI-TERT-BUTYL-4-HYDROXYBENZYL-IDENYL)-INDOLIN-2-ONE ]ACETIC ACID

EXAMPLES 28 TO 30

By subjecting the compounds of Examples 1 to 3 to the action of Lawesson's reagent, the compounds of the following Examples are obtained:

EXAMPLE 27:
6-BROMO-3-(3,5-DI-TERT-BUTYL-4-HYDROX-YBENZYLIDENYL)-1-METHOXYINDOLIN-2-THIONE

EXAMPLE 28:
3-(3,5-DI-TERT-BUTYL-4-HYDROXYBEN-ZYLIDENYL)-6-CHLORO-1-METHOXYINDO-LIN-2-THIONE

EXAMPLE 29:
3-(3,5-DI-TERT-BUTYL-4-HYDROXYBEN-ZYLIDENYL)-1-(2,6-DICHLOROPHENYL)-INDOLIN-2-THIONE

EXAMPLE 30:
6-CHLORO-1-(2,6-DICHLOROPHENYL)-INDO-LIN-2-ONE

The title compound is obtained by proceeding as in Example 1, but replacing the 6-bromo1-methoxyindolin-2-one with 6-chloro1-(2,6-dichlorophenyl)-indolin-2-one.

Example A: STUDY OF THE ANTIPEROXIDISING ACTIVITY OF THE COMPOUNDS OF THE INVENTION The action of the compounds of the invention, capable of trapping .OH radicals, was studied on the one hand in the case of spontaneous peroxidation of lipids and, on the other hand, in the case of peroxidation induced by the system $Fe^{2+}$ ascorbate (10 μM−250 μM), in both instances using rat brain homogenates.

For measurement of the spontaneous peroxidation of lipids, the rat brain homogenates are allowed to stand for 60 minutes at 37° C. in the presence or absence of the compounds to be tested. The reaction is discontinued at 0° C. and the determination of the malonic dialdehyde is carried out using thiobarbituric acid. The lipid peroxidation is determined by the substances that react with thiobarbituric acid expressed in nanomoles of malonic dialdehyde.

For the measurement of the induced lipid peroxidation, the methodology is identical to that described above, with the exception of the addition to the homogenate of the radical-inducing system: $Fe^{2+}$ ascorbate. The reference substances are probucol and vitamin E.

The concentrations of the tested compounds that inhibit the peroxidation of the substrate by 50% are calculated.

It is apparent that the compounds of formula (I) used in accordance with the invention have a particularly intense antiperoxidising activity, since they exhibit an antiperoxidising activity distinctly greater than that of probucol and vitamin E, which is the natural antioxidant of the human organism. This remarkable result is obtained regardless of whether the peroxidation is spontaneous or induced by a chemical system.

Example B: STUDY OF THE PROTECTIVE POWER OF THE COMPOUNDS OF THE INVENTION AGAINST LDL OXIDATION The capacity of the compounds of the invention to decrease the proportions of oxidised LDLs was measured as follows:

Mixtures of native LDLs, a $Cu^{2+}$ system generating free radicals, and the compounds to be tested were incubated for 24 hours.

The results are obtained after analysis of the mixtures by a high performance chromatography method: FPLC (Fast Protein Liquid Chromatography). The protective power of the compound tested is determined by comparison of the chromatogram obtained with that of the positive reference control, probucol.

It is clearly evident that the compounds used in accordance with the invention have a very considerable protective power that is significantly greater than that of probucol and the compounds of U.S. Pat. No. 5,124,347.

Example C: STUDY OF THE INHIBITING ACTIVITY OF THE COMPOUNDS OF THE INVENTION ON THE SYNTHESIS OF PROSTANOIDS

1) STUDY OF THE INHIBITING ACTIVITY ON THE SYNTHESIS OF PROSTANOIDS RESULTING FROM CYCLOOXYGENASE

The aim of this study is to measure the inhibiting activity of the compounds of the invention on the secretion of prostaglandin $E_2$ ($PGE_2$), one of the principal prostanoids produced by the cyclooxygenase of human granulocytes stimulated by the calcium ionophore A23187.

PROTOCOL

Isolation of human granulocytes

Human venous blood from blood donors who have not taken medicaments for 2 weeks is drawn into polypropylene tubes containing 1 volume of anti-coagulant (2.73% citric acid, 4.48% sodium citrate, 2% glucose) per 10 volumes of blood.

In the hour following taking the samples, 6% dextran is added to the blood (0.3 $cm^3/cm^3$ of blood). After incubation for 30 min. at 37° C., the plasma rich in white corpuscles is centrifuged at a speed of 100 g for 5 min. at 4° C.

The sediment is resuspended in 3 $cm^3$ of 0.83% $NH_4Cl$ (in order to lyse the contaminating red corpuscles) and centrifuged at a speed of 100 g for 5 min. at 4° C.

The sediment rich in mono- and poly-nucleated white corpuscles is taken up in 5 $cm^3$ of phosphate buffer (pH 7.4) of the following composition (mM): 137: NaCl, 2.68 : KCl, 8.1 : $Na_2HPO_4$, 1.47 : $KH_2PO_4$, 0.9 : $CaCl_2$, 0.5: $MgCl_2$, and layered on 3 $cm^3$ of a solution of Ficoll 400 having a density of 1.077.

After centrifugation at a speed of 420 g for 30 min. at 4° C., the sediment rich in granulocytes is resuspended in 5 $cm^3$ of phosphate buffer and centrifuged at a speed of 100 g for 5 min. at 4° C. Finally, the granulocytes are counted and the density is adjusted to $3 \times 10^6$ cells/$cm^3$ of phosphate buffer.

Stimulation of granulocytes by the calcium ionophore A23187

The cells ($3 \times 10^6$ cells/$cm^3$) are preincubated at 37° C. for 15 min. in the absence or presence of the products to be tested at the desired concentration. The cells are then stimulated for 15 min. at 37° C. with A23187 at $5 \times 10^{-6}M$ (mother solution at $10^{31}$ $^2M$ in DMSO). The base level is measured using cells without either the products to be tested or A23187.

The reaction is stopped in ice and the supernatant is recovered after centrifugation at a speed of 250 g for 5 min. at 4° C.

Determination of $PGE_2$:

The quantity of $PGE_2$ produced is measured by a radioimmunological assay (RIA). A standardisation scale is produced under the same conditions with normal concentrations of $PGE_2$.

Results

The compounds of the invention exhibit an inhibiting activity on the synthesis of prostanoids resulting from cyclooxygenase that is far greater than that of probucol.

For example, at a concentration of $10^{-5}M$, the compounds of the invention permit an inhibition of the production of $PGE_2$ of 88% whilst probucol causes inhibition only of the order of 40%.

2) STUDY OF THE INHIBITING ACTIVITY ON THE SYNTHESIS OF PROSTANOIDS RESULTING FROM LIPOXYGENASE

The inhibiting activity on the synthesis of prostanoids exhibited by the compounds of the invention is measured using washed human polynuclear cells, in the presence or absence of the compound to be tested, after activation of the cells by calcium (calcium ionophore A 23187).

The production of the principal prostanoid, resulting from lipoxygenase, produced by human polynuclear cells: leucotriene $B_4$ ($LTB_4$) is measured by a radioimmunological assay.

The compounds of the invention exhibit an inhibiting activity on the synthesis of prostanoids resulting from lipoxygenase that is far greater than that of probucol.

For example at a concentration of $10^{-5}M$ the compounds of the invention permit inhibition of the production of $LTB_4$ of more than 95%, whilst probucol causes inhibition only of the order of 40%.

CONCLUSION

Studies 1 and 2 of Example C show that the compounds of the invention have an intense inhibiting activity on the synthesis of prostanoids. That activity is distinctly greater than that of the compounds of U.S. Pat. No. 5,124,347.

Example D: STUDY OF THE ANTI-INFLAMMATORY ACTIVITY OF THE COMPOUNDS OF THE INVENTION

PRINCIPLE

An experimental inflammation, of an immunological nature, is produced by injecting an anti-rat serum into the sole pad of a rat's paw. The inflammatory reaction is exhibited by an oedema of the paw.

The aim of this study is to examine the anti-inflammatory effect of the compounds of the invention in the model of oedema of immunological origin in rats.

The parameters measured are:
the volume of the oedema,
the generation of $E_2$ prostaglandins ($PGE_2$).

PROTOCOL

The animals used in this study are male Wistar rats weighing from 350 to 400 g.

Animals

A localised oedema is produced at time $t_O$ of the study by an intrasole injection of 0.1 $cm^3$ of rabbit anti-rat serum.

Negative control animals are given an intrasole injection of 0.1 $cm^3$ of physiological liquid.

Treatment of the animals

The products are suspended in gum arabic.

One hour before inducing the oedema, the animals receive the products, administered per os, through an oesophageal probe at a dose of from 3 to 30 mg/kg.

Positive control animals, in the same way as the negative controls, receive gum arabic through an oesophageal probe.

Measurement of the volume of the oedema:

The oedema is characterised by the increase in volume of the paw, determined by a water plethysmometer.

An initial measurement of the volume of the paw is carried out before any treatment.

Another measurement is carried out 2 hours after induction of the oedema.

Measurement of PGE$_2$:

The animals are sacrificed directly after the plethysmometer measurement.

The inflamed region is removed and placed in a solution of pH 3.0 containing 33% CH$_3$CN.

After homogenisation, the PGE$_2$ are extracted on a C$_2$ ethyl column (Amersham) and eluted with methyl formate.

After evaporation under nitrogen, the PGE$_2$ are dissolved in 200 µl of phosphate buffer.

The concentrations of PGE$_2$ are measured by radioimmunological analysis.

RESULTS

From a dose of 3 mg/kg, the compounds of the invention appear to permit a very substantial inhibition of the volume of the induced oedema and also bring about a significant reduction in the production of prostaglandin E$_2$, which is one of the major mediators of inflammation.

Example E: ACUTE TOXICITY STUDY

The acute toxicity was evaluated after oral administration to groups each comprising 3 mice (20±2 grams) of increasing doses (0.1, 0.25, 0.50, 0.75, 1 g/kg) of the compounds of the invention. The animals were observed at regular intervals during the course of the first day and daily for 2 weeks following the treatment.

The compounds of the invention appear to be totally non-toxic. No death was observed after administration of a dose of 1 g/kg$^{-1}$. No disorders were ascertained after administration of that amount.

Example F: PHARMACEUTICAL COMPOSITION: TABLETS

Tablets each containing 15 mg of 6-chloro-3-(3,5-di-tert-butyl-4-hydroxybenzylidenyl)1-methoxyindolin-2-one.

Preparation formula for 1000 tablets:

| | |
|---|---|
| 6-chloro-3-(3,5-di-tert-butyl-4-hydroxy-benzylidenyl)-1-methoxyindolin-2-one | 15 g |
| corn starch | 60 g |
| lactose | 45 g |
| magnesium stearate | 0.5 g |
| silica | 0.2 g |
| hydroxypropylcellulose | 0.5 g |

We claim:

1. A compound selected from those of formula (I):

wherein:
X represents sulphur or oxygen,
R$_1$, R$_2$, R$_3$ and R$_4$, which are the same or different, each represents, independently of the others:
  hydrogen,
  or a radical selected from:
    halogen,
    hydroxy,
    a group —E$_1$ or $$-\underset{\underset{O}{\|}}{C}-E_1$$

wherein E$_1$ represents lower alkyl, lower alkenyl, lower alkynyl or lower alkoxy, the group E$_1$ being unsubstituted or substituted by one or more radicals selected from halogen, lower alkyl, lower alkoxy, lower alkylamino and di-lower alkylamino, and a group -(CH$_2$)$_n$-E$_2$, —O—(CH$_2$)$_n$-E$_2$, $$-\underset{\underset{O}{\|}}{C}-(CH_2)_n-E_2, \text{ or } -\underset{\underset{O}{\|}}{C}-O-(CH_2)_n-E_2,$$

wherein n represents 0 or 1 to 4 inclusive and wherein E$_2$ is selected from:
  phenyl and naphthyl, each of which is unsubstituted or substituted by one or more radicals selected from halogen, hydroxy, lower alkyl, lower alkoxy and trifluoromethyl,
  and cycloalkyl having 3 to 8 carbon atoms, inclusive, which is unsubstituted or substituted by one or more radicals selected from halogen, oxo, lower alkyl and lower alkoxy,
R$_5$ represents a radical selected from:
  hydroxy,
  a group —E$_3$ wherein E$_3$ represents lower acyl, lower alkoxy, or a —(CH$_2$)n—CO—R$_6$ group wherein n represents 0 or 1 to 6 inclusive, and R$_6$ represents hydroxy or lower alkoxy, E$_3$ being unsubstituted or substituted by one or more radicals selected from halogen, hydroxy, lower alkyl and lower alkoxy,
  phenyl or —O—(CH$_2$)$_m$-phenyl wherein m represents O or 1 to 4, inclusive, the phenyl nucleus being unsubstituted or substituted by one or more radicals selected from halogen, hydroxy, lower alkyl, lower alkoxy and trifluoromethyl,
  and cycloalkyl or cycloalkyl-lower alkyl, wherein the cycloalkyl radical contains 3 to 8 carbon atoms, inclusive, and is unsubstituted or substituted by one or more radicals selected from halogen, oxo, lower alkyl and lower alkoxy, the terms "lower alkyl", "lower alkoxy" and "lower acyl" mean straight-chain or branched groups containing 1 to 6 carbon atoms inclusive, and the terms "lower alkenyl" and "lower alkynyl" mean unsaturated groups having 2 to 6 carbon atoms inclusive, its Z or E isomers, an optical isomers thereof, and an addition salt thereof with a pharmaceutically-acceptable acid or base.

2. A compound according to claim 1 selected from those wherein $R_5$ represents lower alkoxy, its Z or E isomer, an optical isomer thereof, and an addition salt thereof with a pharmaceutically-acceptable acid or base.

3. A compound according to claim 1 selected from those wherein $R_1$, $R_2$, $R_3$ and $R_4$ are selected from hydrogen, halogen, hydroxy, lower alkyl, lower alkoxy and trifluoromethyl, its Z or E isomer, an optical isomer thereof and an addition salt thereof with a pharmaceutically-acceptable acid or base.

4. A compound according to claim 1 selected from 6-chloro-3-(3,5-di-tert-butyl-4-hydroxybenzylidenyl)-1-methoxyindolin-2-one and its Z or E isomers.

5. A compound according to claim 1 selected from 3-(3,5-di-tert-butyl-4-hydroxybenzylidenyl)-1-(2,6-dichlorophenyl) indolin-2-one and its Z and E isomers.

6. A compound according to claim 1 selected from 3-(3,5-di-tert-butyl-4-hydroxybenzylidenyl)-1-methoxy-indolin-2-one, its Z or E isomer, and its addition salts thereof with a pharmaceutically-acceptable acid.

7. A compound according to claim 1 selected from 6-bromo-3-(3,5-di-tert-butyl-4-hydroxybenzylidenyl)-1-methoxy-indolin-2-one and its Z or E isomer.

8. A pharmaceutical composition comprising as active ingredient a compound according to claim 1, addition salt thereof with a pharmaceutically acceptable in combination with a pharmaceutically-acceptable excipient or carrier.

* * * * *

UNITED STATES PATENT AND TRADEMARK OFFICE
CERTIFICATE OF CORRECTION

PATENT NO. : 5,382,593
DATED : January 17, 1995
INVENTOR(S) : Guillaume Le Baut et. al.

It is certified that error appears in the above-indentified patent and that said Letters Patent is hereby corrected as shown below:

TITLE PAGE, ITEM [30]; "92.8951" should read -- 92.08951 --
Column 3, line 47; "campboric" should read -- camphoric --

Column 7, line 6; insert a space between "v" and the "in"

Column 10, line 33; "6-bromol-" should read -- 6-bromo-1- --
Column 10, line 54; "6-bromol-" should read -- 6-bromo-1- --
Column 13, line 11; insert a space between "v" and "cm"

Column 13, line 39; "6-bromol-" should read -- 6-bromo-1- --

Column 14, line 20; "6-bromol-" should read -- 6-bromo-1- --
Column 14, line 21; "6-chlorol-" should read -- 6-chloro-1- --
Column 15, line 29; insert a ":" after "granulocytes"
Column 15, line 57; insert a ":" after "A23187"
Column 15, line 62; "$10^{312}M$" should read -- $10^{-2}M$ --
Column 16, line 5; insert ":" after the word "Results"
Column 16, line 61; insert ":" after the word "Animals"
Column 16, line 67; insert ":" after the word "animals"

UNITED STATES PATENT AND TRADEMARK OFFICE
CERTIFICATE OF CORRECTION

PATENT NO. : 5,382,593
DATED : January 17, 1995
INVENTOR(S) Guillaume Le Baut et. al.

It is certified that error appears in the above-indentified patent and that said Letters Patent is hereby corrected as shown below:

Column 17, line 54; ")1-methoxyindolin-" should read -- )-1-methoxyindolin- --

Column 19, line 8; "isomers" should read -- isomer --

Column 20, line 5; "isomers" should read -- isomer --

Column 20, line 8; "Z and E" should read -- Z or E -- also "isomers" should read -- isomer --

Column 20, line 17; delete the letters "addi-"

Column 20, line 18; delete the words "tion salt thereof with a pharmaceutically acceptable"

Signed and Sealed this

Eighteenth Day of July, 1995

Attest:

BRUCE LEHMAN

Attesting Officer    Commissioner of Patents and Trademarks